United States Patent [19]
Coxon et al.

[11] Patent Number: 6,104,029
[45] Date of Patent: Aug. 15, 2000

[54] SPECTROMETER AND METHOD OF SPECTROSCOPY

[75] Inventors: Peter Coxon, Buxted; Bryan Barnard, London; H. Sebastian Von Harrach, Tunbridge Wells, all of United Kingdom

[73] Assignee: VG Systems Ltd., United Kingdom

[21] Appl. No.: 09/139,198

[22] Filed: Aug. 25, 1998

[30] Foreign Application Priority Data

Aug. 26, 1997 [GB] United Kingdom .................... 9718012

[51] Int. Cl.⁷ ...................................................... H01J 47/00
[52] U.S. Cl. ........................................ 250/305; 250/396 R
[58] Field of Search ................................ 250/305, 396 R, 250/397

[56] References Cited

U.S. PATENT DOCUMENTS

| 4,764,673 | 8/1988 | Bryson, III et al. | 250/305 |
| 4,823,003 | 4/1989 | King et al. | 250/305 |
| 5,285,066 | 2/1994 | Sekine et al. | 250/305 |
| 5,506,414 | 4/1996 | Coxon | 250/305 |

FOREIGN PATENT DOCUMENTS

| 0 246 841 | 11/1987 | European Pat. Off. . |
| 2 064 213A | 6/1981 | United Kingdom . |
| 2 244 369A | 11/1991 | United Kingdom . |
| WO 81/03395 | 11/1981 | WIPO . |

OTHER PUBLICATIONS

D. Roy, D. Tremblay, B. Tremblay, D. Dube, "A New Multidetection Spectrometer for Studies of Angle–Resolved Electron Distributions", Journal of Electron Spectroscopy and Related Phenomena 52, 1990, pp. 787–796.

A. Bosch, H. Feil, G.A. Sawatzky, "A Simultaneous angle–resolved photoelectron spectrometer", Journal of Physics E: Scientific Instruments, vol. 17, 1984, pp. 1187–1192.

N.K. Krasnova, S.N. Davydov, Y.K. Golikov, V.V. Korablev, Y.A. Kudinov, "Cone electrostatic energy analyser, used for concurrent energy–and angle resolved meansurements", Journal of Electron Spectroscopy and Related Phenomena 72, 1995,pp. 323–326.

H.A. Engelhardt, W. Back, D. Menzel, H. Liebl, "Novel charged particle analyzer ffor momentum determination in the multichanneling mode: I. Design aspects and electron/ion optical properties", Review Scientific Instruments, vol. 52, No. 6, 1981, pp. 835–839.

D. Varga, K. Tokesi, I. Rajta, "Design of an Electrostatic Electron Spetrometer for Simultaneous Energy and Angular Distribution Measurements", Journal of Electron Spectroscopy and Related Phenomena 76, 1995, pp. 433–436.

D.E. Eastman, "Angle–Resolved Electron Spectrometer with Large–Angle Visual Display", IBM Technical Disclosure Bulletin, vol. 22, No. 6, 1979, pp. 2561–2562.

R.G.C. Leckey, J.D. Riley, "A Toroidal Angle Resolving Electron Spectrometer for Surface Studies", Applications of Surface Science, vol. 22/23, 1985, pp. 196–205.

(List continued on next page.)

*Primary Examiner*—Kiet T. Nguyen
*Attorney, Agent, or Firm*—Thomason, Moser & Patterson LLP

[57] ABSTRACT

A spectrometer and method of spectroscopy are provided for surface analysis. The spectrometer comprises an energy analyser for analysing the energies of charged particles liberated from a sample, a lens arranged to project a diffraction image of the analysis area at the image plane of the lens and a detector for detecting the charged particles. The analyser and lens are arranged to generate an image at the detector in which the charged particles are distributed along a first direction according to their emission angles and are distributed along another direction according to their energies. The detector is arranged to detect the distribution of charged particles in the image along the first direction to provide angle resolved energy spectra.

44 Claims, 6 Drawing Sheets

OTHER PUBLICATIONS

U. Gelius, B. Wannberg, P. Baltzer, H. Fellner–Feldegg, G. Carlsson, G–C Johansson, J. Larsson, P. Munger, G. Vegerfors, "A New Esca Instrument with Improved Surface Sensitivity, Fast Imaging Properties and Excellent Energy Resolution", J. of Electron Spectroscopy and Related Phenomena, vol. 52, 1990, pp. 747–785.

M. Kato, T. Sekine, "Spherical Abberation Correction of Electrostatic Lenses using Spherical Meshes", Journal of Vacuum Science Technology A, vol. 13(4), Jul./Aug. 1995, pp. 2255–2260.

Technical Data Sheet–GAMMADATA, Jun. 13, 1997.

D.E. Eastman, J.J. Donelon, N.C. Hein, F.J. Himpsel, "An Ellipsoidal Mirror Display Analyzer System for Electron Energy and Angular Measurements", Nuclar Instrumentation and Methods 172, 1980, pp. 327–336.

F. Tofelleto, R.C.G. Leckey, J.D. Riley, "Design Criteria for an Angle Resolved Electron Spectrometer of Novel Toroidal Geometry", Nuclear Instruments and Methods in Physics Research, vol. B12, 1985, 282–297.

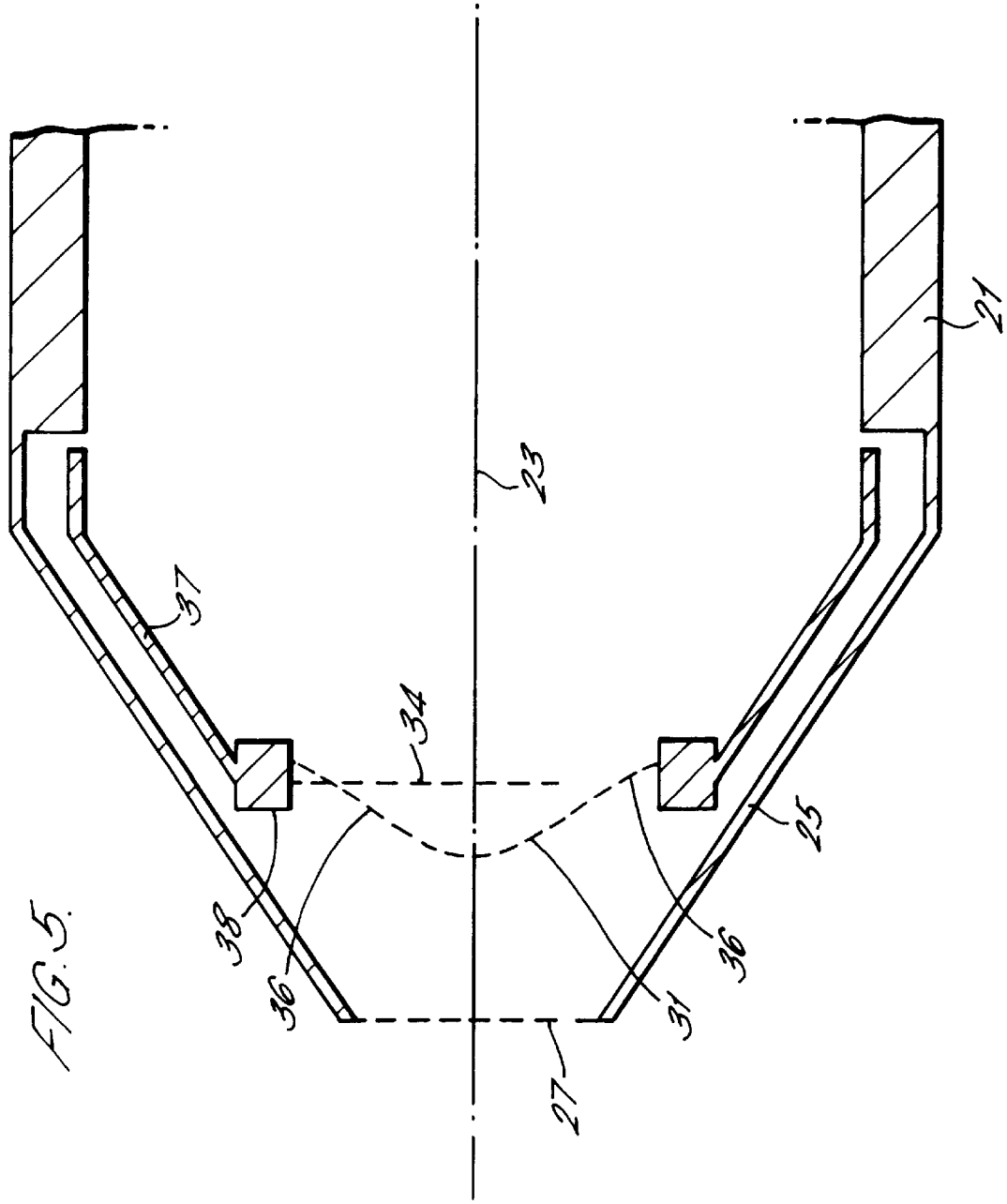

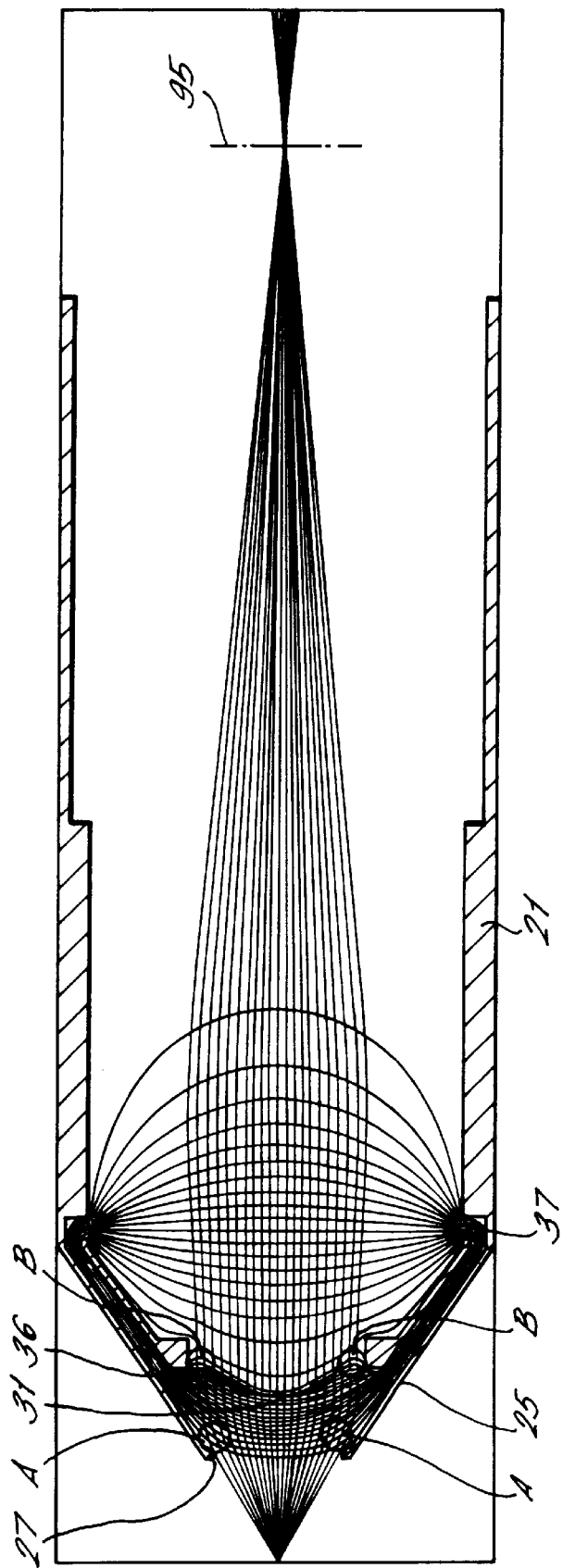

SPECTROMETER AND METHOD OF SPECTROSCOPY

FIELD OF THE INVENTION

This invention generally relates to spectroscopy and in particular relates to spectrometers and methods of spectroscopy for surface analysis of solid samples. This invention also relates to lenses for use in such spectrometers.

DISCUSSION OF PRIOR ART

In surface science, spectroscopy can provide a powerful tool for analysing the surface and near-surface chemical constituents of solid objects. Surface spectroscopy commonly involves irradiating a selected area of a surface with a beam of radiation or particles to release secondary particles from the surface of the irradiated area which can then be analysed to determine the chemical species from which they derive.

Commonly used spectroscopy techniques for surface studies include X-ray photoelectron spectroscopy (XPS or ESCA) and Auger electron spectroscopy (AES). The former technique involves irradiating a surface with a beam of X-rays of a preselected energy to release atomic core electrons from the chemical elements at or near the surface and measuring their energies. Since the binding energy of the core electrons is unique for each element and can be measured by measuring the difference between the photon and electron emergent energies, the surface elements can be readily identified. Auger electron spectroscopy is based on a similar principle as XPS except that the primary beam comprises a moderately energetic beam of electrons of about 2–25 keV and the secondary electron energies are independent of the incident electron energy.

In X-ray photoelectron spectroscopy, the energies of electrons emitted from the surface are such that the electrons have very short in-elastic mean free paths of for example 0.1 to 5 nm, in solid samples. Therefore, the angle of emergence of electrons from the surface provides additional information as to the depth of the chemical constituent with those electrons emitted at grazing angles being released from the uppermost atomic or molecular layers. Thus, by detecting the angles of electron emergence and their energy spectra a depth profile of the surface constituents can be measured.

In order to derive the depth profile efficiently, it is highly desirable to measure the energy spectra over a range of emergence angles simultaneously and a number of spectrometer designs have been proposed to achieve this. One design, for example described by Tofelletto et al in Nuclear Instruments and Methods, Physics Research B12 (1985), pages 282–297 and by R. C. G. Leckey et al, Applications of Surface Science, Vols. 22/23 (1995), pages 196–205 comprises an energy analyser having a toroidal geometry, an axially symmetric zoom input lens mounted centrally within the torus for focusing particles at the entrance of the toroidal section and adjusting their energies to the pass energy of the analyser, an axially symmetric conical output lens and a position sensitive detector. Electrons from a sample located within the centre of the torus emitted radially over a range of angles are collected by the input lens, energy analysed and form a ring image on the position sensitive detector, such that each polar position on the detector corresponds to a unique electron emission angle from the sample. One drawback of this instrument is that the central space within the torus offers both limited space for mounting the sample and poor sample accessibility.

Another example of a spectrometer which is capable of measuring both energy and angular distributions of electrons simultaneously over the full range of surface scattering angles is described by D. Varga et al in Journal of Electron Spectroscopy and Related Phenomena, Vol. 76 (1995), pages 433–436. The spectrometer comprises a double-pass cylindrical mirror analyser (CMA) having focusing electrodes with conical ends which shape the electric field so that electrons emitted at 90° to the CMA axis enter the second pass CMA at an angle of less than 90° and are focused by the second stage into a ring. A position sensitive detector at a ring focus is used to measure the angular distribution of electrons in the full azimuthal range at a given energy. Whereas this design increases the acceptance angle of conventional CMAs, the sample has to be placed within the restricted volume of the CMA which therefore places an upper limit on the size of sample that can be analysed by this instrument and severely limits access to the sample.

H. A. Englelhardt et al, Review Scientific Instruments, Vol. 52, No. 6 (1981), pages 835–839 describes a toroidal capacitor energy analyser which is designed to measure the energy spectra of electrons over a range of emission angles simultaneously. No input lens is used in this arrangement in order to increase the field-free space between the sample and analyser input. The field-free region is established by a grounded electrode immediately in front of the analyser input aperture and which defines a rotationally symmetric input slit about the toroidal axis which is very narrow in the energy dispersive direction. The input slit is arranged to accept electrons emitted from a sample placed on the toroidal axis over electron emission angles ranging from zero to 90° to the sample surface. A truncated conical output lens focuses electrons passed by the analyser onto a position sensitive detector. The electron image forms a ring concentric with the toroidal axis. The angular position on the ring corresponding to the polar angle of emission from the surface of the sample is preserved by the field-free region. One drawback of this arrangement is that the input slit only accepts electrons from a very thin azimuthal segment, limiting the sensitivity of the instrument. Furthermore, the axial location for the sample restricts its accessability.

A retarding field analyser for angle-resolved photoelectron spectroscopy is described by D. E. Eastman et al, Nuclear Instruments and Methods, Vol. 172 (1980), pages 327–336. An elliptical retarding grid acting as a low pass energy filter and a spherical retarding grid acting as a high pass energy filter are used to form both energy and angular analyses. Electrons below a predetermined energy emitted over a range of angles from a source positioned at a focal point of the elliptical grid are reflected to its other focal point which coincides with the focal point of the spherical grid. Electrons above a predetermined energy are transmitted through a series of grids, which form the spherical high pass filter stage, onto a two-dimensional position sensitive detector, each position corresponding to an emission angle from the sample surface. While achieving simultaneous angular resolution over a wide range of emission angles, this instrument, being of the retarding field type, gives relatively poor energy resolution as compared to other forms of spectrometer and is not particularly suitable for large, flat samples.

A conventional double pass CMA has been modified to measure angle resolved electron emission spectra simultaneously as for example described by A. Bosch et al, Journal of Physics E: Scientific Instruments, Vol. 17 (1984), pages 1187–1192. In this instrument, the sample surface is placed at an angle to the cylinder axis so that the conical distribution of electrons accepted by the CMA contains electrons emitted over a range of angles. A two-dimensional position detector is placed behind the output plane of the CMA for detecting the angle resolved spectra. Although the energy resolution of this instrument improves upon that of the spectrometer described by Eastman et al and the CMA has a large acceptance angle, the two-dimensional image at the detector is relatively difficult to interpret in terms of simple energy-angle co-ordinates.

N. K. Krasnova et al, Journal of Electron Spectroscopy and Related Phenomena, Vol. 72 (1995), pages 323–326 describes a conical electrostatic energy analyser for simultaneous measurement of multiple angular resolved emission spectra. The instrument comprises inner and outer coaxially arranged conical electrodes of different cone angle with the inner electrode defining input and output slits for passing electrons emitted from a sample surface positioned on the cone axis. Electrons are energy resolved by the field between the two electrodes in the radial direction and are detected by a position sensitive detector positioned on the other side of the output aperture transverse to the cone axis. The angular distribution of electrons from the sample surface in an emission plane transverse to the cone axis is preserved and corresponds to the angular distribution at the detector. A disadvantage of this arrangement is that electrons at energies above and below the centre energy are not focused at the detector and there is relatively poor access to the surface of the sample.

A spectrometer for angle-resolved photoelectron spectroscopy having multiple discrete electron detectors is described in D. Roy et al, Journal of Electron Spectroscopy and Related Phenomena, Vol. 52 (1990), pages 787–796. The spectrometer comprises a truncated spherical mirror in the centre of which is a location for a gas-phase sample. Nineteen collimators distributed radially about the symmetry axis pass electrons scattered at discrete angular intervals into the spherical mirror analyser. The angle and energy resolved electrons are detected by nineteen channel electron multipliers, again distributed radially around the symmetry axis. Although this design allows angular resolved energy spectra to be measured in parallel, the multiplicity of collimators and channel electron multipliers make the instrument relatively complex and do not allow the continuous angular distribution to be measured. Furthermore, the instrument is not suitable for surface studies of relatively large samples.

Electron spectrometers for surface studies which use hemispherical sector analysers (HSA) are described in U. Gelius et al, Journal of Electron Spectroscopy and Related Phenomena, Vol. 52 (1990), pages 747–785, EP-A-0246841 and GB-A-2064213. The instruments described in these references have an electron lens system in front of the input plane of the HSA so that the sample can be removed from the vicinity of the analyser, thereby allowing good access to the sample area. These spectrometers are designed to image energy spectra over a selected analysis area of the sample surface. In the instrument described by Gelius et al, a beam of X-rays from a monochromatic source, causes photoelectron emission from a spot on the sample surface defining an object which is magnified by the electron lens and imaged onto the input plane of the HSA. A narrow slit at the input plane whose width is in the energy dispersive direction of the analyser passes electrons into the analyser which projects a two-dimensional image onto the image plane with energy spectra along the dispersive direction and a spatial dimension along the non-dispersive direction. Thus, energy spectra from each point on a line of the analysis area are captured in parallel. To obtain a two-dimensional spatial image of the energy spectra, the sample is rastered in the other, orthogonal direction. Deflector plates are incorporated into the electron lens system to move the position of the area giving an image at the analyser input slit thus providing a means of scanning over the X-ray spot without mechanical manipulation of the sample. In order to measure the angular distribution of energy spectra, the sample is tilted successively at different angles to the lens axis.

The spectrometer disclosed in EP-A-246841 includes a pre-analysis lens system which projects a diffraction image of the analysis area onto the object plane of the analyser which forms a spectral image in the analyser image plane which is substantially independent of spatial features of the analysis area. A second lens beyond the image plane of the analyser forms a second diffraction image from the energy dispersed image at the analyser image plane, this second diffraction image being a spatial image of the sample surface which is independent of the energy dispersion from the analyser image plane.

The pre-analysis lens system disclosed in GB-A-2064213 comprises an aberration compensating lens element for collecting electrons over a relatively large half-cone angle of between 25° and 30° and a zoom lens element which both retards electrons to the pass energy of the hemispherical sector analyser and focuses a magnified spatial image of the analysis area at the input plane of the HSA. The aberration compensating lens comprises a pair of mesh elements which are concave towards the sample and provide a retarding field therebetween to refract the divergent electrons towards the lens axis. The spherical mesh arrangement allows spherical aberration, which would affect the most divergent electrons in a coaxial tubular lens system, to be reduced so that the lens can collect and focus electrons over a relatively large solid angle.

The use of mesh elements for reducing spherical aberration in electron lenses has been analysed by M. Kato and T. Sekine, Journal of Vacuum Science Technology A 13(4) (1995), pages 2255–2260, in which an electron lens design is disclosed having a mesh element configured in a similar way to the mesh elements disclosed in GB-A-2064213.

As noted above, electron spectrometers which are capable of measuring electron energy spectra simultaneously over a range of emission angles without rotating the sample are known but these instruments suffer from poor energy resolution, poor sample accessibility, are relatively complex and/or the measurements cannot easily be interpreted. Other spectrometers are known which have good energy resolution and sample accessibility and provide energy spectra and spatial imaging of the surface. However, these instruments do not allow the simultaneous measurement of angle resolved spectra, it being necessary to rotate the sample to make successive measurements of the energy spectra at different emission angles. Furthermore, such rotation causes the analysis area to change so that energy spectra obtained from different emission angles cannot unequivocally be attributed to the same surface coordinate. Therefore it would be highly desirable to design a spectrometer capable of measuring angle resolved spectra in parallel without the drawbacks of the prior art instruments.

SUMMARY OF THE INVENTION

According to one aspect of the present invention there is provided a spectrometer comprising an energy analyser for analysing energies of charged particles emitted from an analysis area of a sample, a lens arranged to project a diffraction image of at least part of said analysis area at the image plane of said lens, and a detector for detecting said charged particles, wherein said analyser and lens are arranged to generate an image at said detector in which said charged particles are distributed along a first direction of said image according to their emission angles and said charged particles are distributed along another, second direction of said image according to their energies, said detector being arranged to detect the distribution of charged particles along said first direction.

Also according to this aspect of the present invention there is provided a method of measuring energy spectra of charged particles emitted from a surface over a range of emission angles comprising, the steps of (a) forming a diffraction image of said charged particles, (b) resolving said charged particles spatially according to their energies, where steps (a) and (b) are performed in either order and (c) forming an image of said charged particles in which said charged particles are distributed in a first direction according to their emission angles and in another, second direction according to their energies, and (d) deriving from said image angle-resolved energy spectra of said charged particles.

In one embodiment, the energy analyser has an object plane, an image plane, and an energy dispersive axis, and the lens is arranged to project said charged particles onto said object plane as a real image of at least part of said analysis area substantially in the direction of said axis and as a diffraction image of said at least part of said analysis area substantially along a non-dispersive direction of said analyser.

A spectrometer according to this arrangement resolves the angular distribution of charged particles from the analysis area spatially along a non-energy dispersive direction of the analyser and, at the same time generates a spatial image of the analysis area in the energy dispersive direction. Charged particles entering the analyser are energy resolved in one direction while the spatially translated angular information is preserved in the other direction so that a two-dimensional image can be formed at the analyser image plane containing energy spectra along the energy dispersion axis for each of a plurality of emission angles distributed along the non-energy dispersive direction. Advantageously, this spectrometer design allows energy spectra to be measured over a range of emission angles simultaneously and in which the image at the analyser output plane can easily be interpreted.

In a preferred embodiment, the energy analyser comprises a hemispherical sector analyser with unit magnification so that there is one-to-one correspondence between the diffraction image at the analyser object plane and that at the analyser image plane.

Preferably, the energy analyser defines an input slit having a narrow width in the energy dispersive direction.

The lens may comprise an electrostatic lens which includes first and second opposed electrodes spaced apart also in a direction transverse to the lens axis and third and fourth opposed electrodes spaced apart in a direction transverse to the lens axis and being generally orthogonal to said first and second electrodes. Preferably, the lens includes further electrode means spaced from each end of said first, second, third and fourth electrode means along said lens axis. Advantageously, such an arrangement combines a quadrupole lens with a three element Einzel lens in a simple and compact construction. In one embodiment, at least one of the first and third electrode means can be biased to a different potential to that of its respective opposed second and fourth electrode means to enable the analysis area to be scanned.

Preferably, the spectrometer further comprises an objective or transfer lens disposed before said lens for producing a real, magnified image of said analysis area for said lens.

Preferably, the transfer lens comprises an input aperture for receiving a divergent stream of charged particles from the analysis area and a mesh electrode disposed upstream of said input aperture and defining a surface portion arranged to converge towards the lens axis in a direction towards the input aperture. Advantageously, the inclined surface defined by the mesh allows an electric field to be established between the mesh and a sample which accelerates emitted charged particles and at the same time provides focusing, thereby reducing chromatic aberration of the lens in comparison with the known retarding lens design, and improving the performance of the spectrometer.

Thus, according to another aspect of the present invention, a lens for collecting and focusing a divergent stream of charged particles comprises means defining an input aperture for receiving said divergent stream, a lens axis extending through said input aperture, first electrode means, second electrode means spaced from said first electrode means along said lens axis comprising a multi-apertured electrically conductive web arranged to allow charged particles in said stream to pass therethrough, wherein a portion of the surface of said electrically conductive web is spaced from and arranged to converge towards said lens axis in a direction towards said input aperture thereby to provide an electric field component which opposes divergence of said stream when a potential difference is applied between said first and second electrode means to accelerate said charged particles towards said second electrode means.

BRIEF DESCRIPTION OF THE DRAWINGS

Examples of embodiments of the present invention will now be described with reference to the drawings, in which:

FIG. 5 shows an exploded view of part of the objective lens shown in FIG. 4; and FIG. 6 shows a two-dimensional ray diagram of charged particle trajectories through an embodiment of the objective lens.

DESCRIPTION OF PREFERRED EMBODIMENTS

Figure 1:
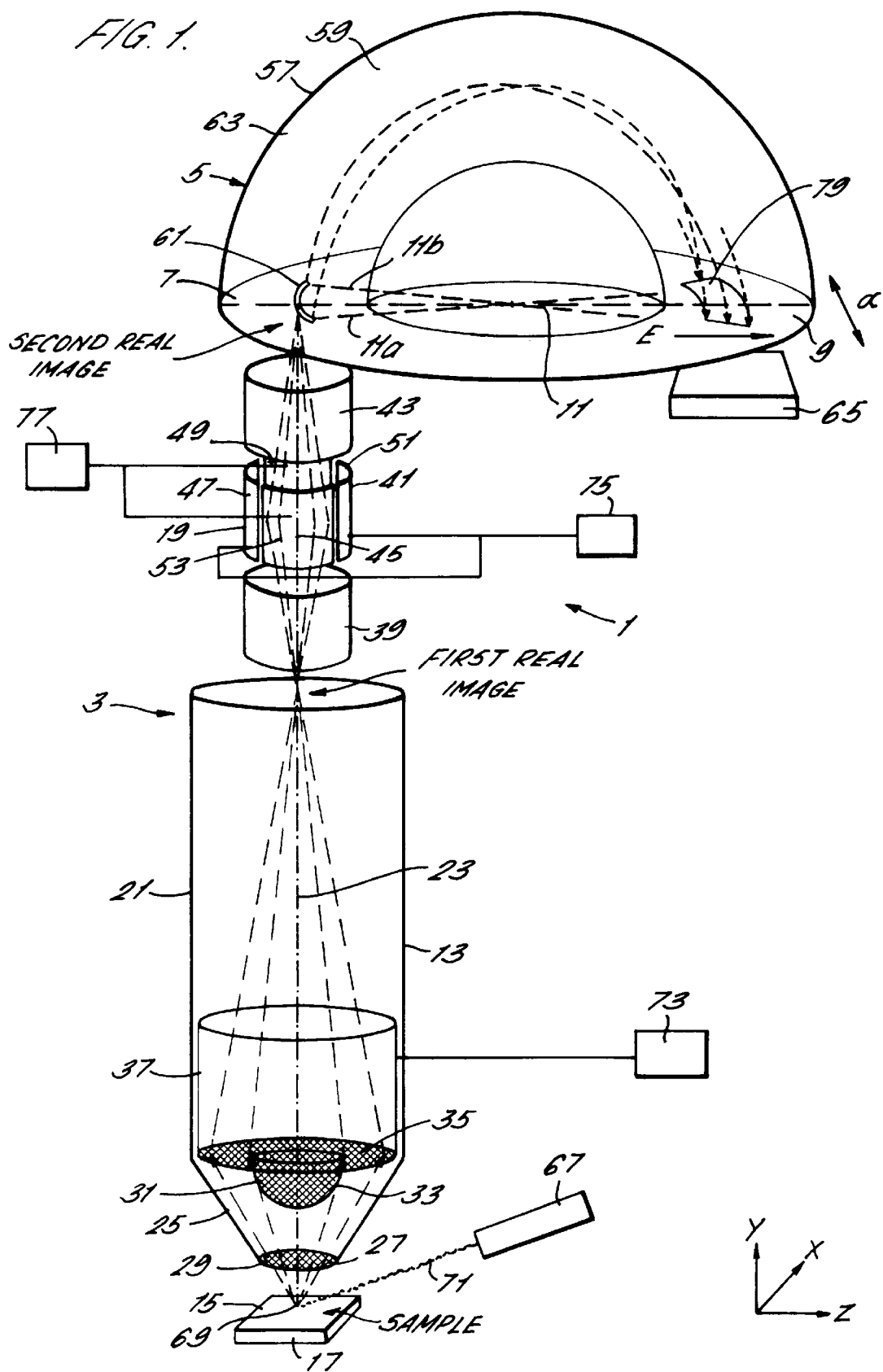
FIG. 1 shows a perspective view of a schematic of an embodiment of the invention.
Figure 2:
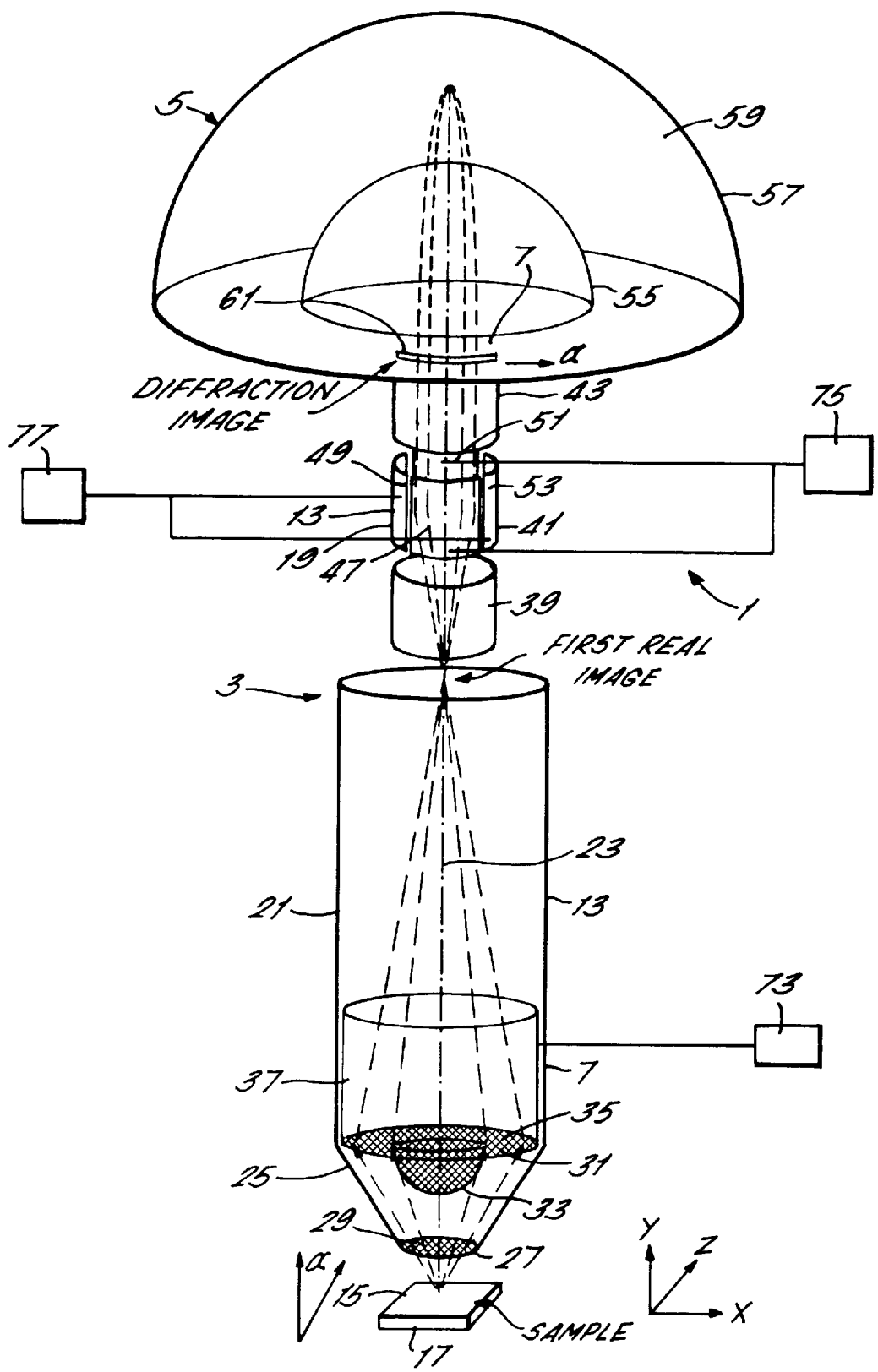
FIG. 2 shows another perspective view of the embodiment shown in FIG. 1.

Referring to FIGS. 1 and 2, in which the same reference numerals are used to designate like parts, a spectrometer generally shown at 1 comprises a pre-energy analysis lens apparatus 3 and a hemispherical sector analyser 5. The energy analyser 5 has an object or input plane 7, an image or output plane 9 and an energy dispersive axis 11. The pre-analysis lens apparatus 3 comprises a first or objective lens 13 for collecting and focusing charged particles emitted from the surface 15 of a sample 17 over a range of emission angles α and a second lens 19 disposed downstream of the objective lens 13 for projecting charged particles onto the object plane 7 of the analyser 5 as a real image of part of the sample surface in the direction of the energy dispersive axis 11 and as a diffraction image of part of the sample surface along a non-energy-dispersive direction of the analyser.

The objective lens 13 comprises a cylindrical electrode 21 whose axis 23 defines the lens axis, and a coaxial truncated conical section 25 tapering towards and defining a lens input aperture 27. A flat mesh 29 is mounted over the lens input aperture 27. The objective lens 13 further comprises a mesh electrode 31 mounted downstream of the input aperture 27 and having a convex section 33 directed towards the input aperture 27. The convex section 33 is preferably rotationally symmetric about the lens axis 23 and has a curvature which may for example be spherical or parabolic. The mesh electrode 31 further includes an outer annular section 35 positioned away from the lens axis 23 and adjoining the convex section 33 and which defines a substantially planar surface transverse to the lens axis 23. A further cylindrical electrode 37 is coaxially mounted within the outer cylindrical electrode 21 and adjoins the outer perimeter of the annular section 35 of the mesh electrode 31, extending upstream thereof and partway along the length of the outer cylindrical electrode 21. The mesh electrode 31 and inner cylindrical electrode 37 are electrically connected together and electrically isolated from the outer cylindrical electrode 21, the frusto-conical section 25 and the flat mesh 29 across the input aperture 27.

The second lens 19 comprises three axially spaced cylindrical electrode sections 39, 41, 43 defining a second lens axis 45 which is coaxially aligned with the objective lens axis 23. The centre electrode section 41 comprises four discrete electrodes 47, 49, 51, 53 with adjacent electrodes being separated along a line parallel to the lens axis 45 and each forming substantially equal segments of a cylinder and each being symmetrically disposed within a respective cylinder quadrant. Two of these electrode segments 47, 51 are diametrically opposed in the direction of the energy dispersion axis of the hemispherical energy analyser 5 and the other two electrode segments 49, 53 are diametrically opposed in a direction normal thereto, i.e. in a non-energy-dispersive direction of the analyser 5.

The hemispherical energy analyser 5 comprises two concentric hemispherical electrodes 55, 57 defining a hemispherical space 59 therebetween. An input aperture 61 is formed at the analyser object plane 7. The input aperture 61 is formed as an arcuate slit whose centre of curvature coincides with the spherical centre 63 of the analyser 5, with the slit lying on a circle whose radius is substantially midway between the inner and outer electrodes 55, 57. The analyser further comprises a two-dimensional position detector 65, for example a two-dimensional multi-channel detector, positioned adjacent the analyser output plane 9 for detecting the two-dimensional angle resolved spectral image of the sample produced by the spectrometer.

An example of a method of operating the spectrometer will now be described, in which, for the purposes of illustration, the spectrometer is used to perform X-ray photoelectron spectroscopy of a sample surface. Referring again to FIGS. 1 and 2, a source of X-rays 67 is provided and arranged to irradiate a predefined area 69 with a beam of X-rays 71. The X-ray source preferably has the capability of focusing the beam of X-rays 71 to form a spot defining the analysis area whose size can be varied from, for example, diameters of 0.5 mm and below. The source may comprise a source of $ALK\alpha$ X-rays provided by a quartz crystal monochromator.

The sample is mounted on a support which preferably comprises a manipulator arranged to scan the sample in directions transverse to the lens axis. The sample support may also be arranged to allow the angle of tilt between the sample surface and/or the distance along the lens axis between the sample surface and the objective lens to be varied.

The sample is positioned at a distance in front of the input aperture 27 of the objective lens such that the lens can collect electrons liberated from the sample surface in a solid cone of relatively large semi-angle, for example 25° to 30°. To obtain angular rather than spatial information from the sample it is necessary to restrict the surface area from which electrons are collected by the spectrometer such that the area approaches a point source. Therefore, to obtain electron energy spectra over a large range of emission angles it is only necessary for the X-ray source to irradiate a very small area. Preferably, the focused X-ray spot on the sample surface is aligned with the lens axis, although, as will be explained below, such alignment is not critical in this instrument.

The convex mesh electrode element 31 is biased positively with respect to the conical section 25 and the flat mesh input aperture 29 by a suitable voltage biasing means 73, thereby defining an accelerating field component between the lens input aperture 27 and the convex mesh element 31 and an electric field component transverse to the lens axis which opposes divergence of the electron stream. This arrangement is in marked contrast to prior art spherical mesh lenses in which the mesh lens elements are concave towards the sample surface and which are biased to retard the electron stream. Although the use of such spherical meshes are known to reduce spherical aberration, the present arrangement not only reduces spherical aberration so that a widely divergent stream of charged particles can be focused with acuity but also reduces chromatic aberration, thereby improving the performance of the instrument. This is achieved by designing the lens to operate with a lens constant, defined by the ratio, $\beta$, of the potential difference between the convex mesh lens and the sample surface and the electron energy, of greater than 1. In other words, the lens is arranged to accelerate charged particles emitted from the sample surface towards the convex mesh lens. This has the effect of decreasing the variance $\Delta E$ in electron energies as a percentage of the centre pass energy E of the lens. The lens constant $\beta$ may have any value greater than 1 and preferably $\beta>2$.

Preferably, the region between the sample surface 15 and the lens input aperture 27 has no electric field therebetween which is achieved by maintaining the outer surfaces of the objective lens in the vicinity of the sample at the same potential as the sample which may conveniently be ground potential. In particular, the frusto-conical section 25 is maintained at ground potential. The flat mesh element 29 across the aperture 27 which is entirely optional enhances the screening between the convex electrode element 31 and the sample to extend the field-free region substantially to the input aperture 27 and also serves to shape the electric field between the convex mesh element 33 and the lens input aperture 27. The provision of a field-free region between the sample and lens input aperture facilitates the transport of low energy electrons to neutralise the surface of insulating samples during analysis.

The planar, annular mesh element 35 surrounding the convex element 31 weakens the focusing effect on electrons travelling near the edge of the stream in the space adjacent the mesh element to correct for spherical aberration.

A potential difference is established between the outer cylindrical electrode 21 and the inner cylindrical electrode 37 such that the potential of the inner cylindrical electrode 37 is greater than that of the outer cylindrical electrode. Conveniently, the outer cylindrical electrode may be maintained at the same potential as the conical section 25, e.g. at ground potential. The potential difference between the inner and outer cylindrical electrodes 37, 21 form an electric field which focuses the electron stream. The objective lens is arranged to project the electrons onto its image plane as a first real, magnified image $I_1$ of the analysis area. In a preferred arrangement, the objective lens magnifies the object by about five times although the magnification may be increased or decreased above or below this value. Magnification by the objective lens is an important requirement since this reduces the cone angle of the electron stream entering both the second lens 19 and the input slit 7 of the energy analyser 5 so as to increase the number of electrons admitted into the analyser to improve its sensitivity.

The second lens is constructed and operated to project a second real image $I_2$ of the first real image $I_1$ onto the image plane 7 of the energy analyser 5 in the energy dispersive direction and to project a diffraction image of the first real image onto the analyser image plane 7 in a non-energy-dispersive direction. This can be achieved by applying appropriate potentials to the quadrant electrodes 47, 49, 51, 53 of the middle electrode section 41 so that the lens has different focusing properties in orthogonal directions mutually perpendicular to the lens axis. The requirement of a real image and orthogonal diffraction image coinciding with the input plane of the energy analyser can be met if the focal length $F_e$ in the object space of the second lens in the energy dispersive direction is such that the first real image $I_1$ coincides with a point at twice the focal length of the second lens in the energy dispersive direction, i.e. $2F_e$ and the focal length $F_n$ in the object space of the second lens in the orthogonal, non-energy-dispersive direction is such that a point on the lens axis at $F_n$ also coincides with the first real image $I_1$. Under these conditions, the second lens will project a second real image of the analysis area onto the analyser input plane 7 in the energy dispersive direction, the second lens having unit magnification. Thus, the second lens translates the distribution of emission angles along a single spatial axis so that each point on the line corresponds uniquely to a discrete emission angle and projects this diffraction image onto the input plane of the energy analyser in the non-energy-dispersive direction so that the spatially dispersed distribution of emission angles is preserved in the analyser object plane.

This asymmetric focusing of the second lens is established by applying a first potential to the opposed electrode elements 47, 51 by a suitable biasing means 77 and a second potential to the opposed electrodes elements 49, 53 by a suitable voltage biasing means 79 of smaller magnitude than the first potential. For example, the first potential may be about four to five times the electron energy and the second potential may be three to four times the electron energy.

The energy resolution of the hemispherical energy analyser 5 increases with decreasing pass energy and the pass energy, which is controlled by the potential difference between the inner and outer hemispherical electrodes 55, 59, is set to the desired value. In order to measure the energy spectra of electrons above the analyser pass energy it is necessary to retard the electrons prior to entering the analyser and in the present embodiment a retarding field is applied to the electrons just in front of the analyser input plane. In a preferred embodiment, the retarding field is established between two mesh electrodes (not shown in FIGS. 1 and 2) one of which is placed in front of the input slit 61 and the other being placed substantially at the input slit 61. The mesh nearest the input slit is biased negatively with respect to the other mesh which is preferably at the same potential as the final electrode element 43 of the second lens 19 and the hemispherical electrode elements 55, 57 of the analyser 5 are floated relative to the negatively biased mesh.

As mentioned above, the second lens projects a line image onto the input plane of the energy analyser and is aligned with the arcuate input slit 61. The hemispherical energy analyser 5 has unit magnification and focuses in both radial and circumferential directions (i.e. is double-focusing). The hemispherical geometry of the analyser provides an energy dispersive axis for each point along the slit, all of which pass through the spherical centre 63. The slit is formed on the arc of the circle rather than in a straight line so that the distance from the centre of the analyser to a point on a radius at the image plane corresponds directly to the electron energy irrespective of the azimuthal angle of the radius. Alignment of the line image with the arcuate input slit is accomplished by orienting the line image in a direction substantially perpendicular to a radius from the centre of the analyser passing through the centre of the arc defined by the slit 61 and which corresponds to the energy dispersion axis 11. The line image may also be positioned so that electrons are emitted over as much of the length of the slit as possible to maximise the range of emission angles over which energy spectra are measured. The input slit is typically 1 mm to 2 mm wide by 15 mm to 25 mm long and the width partially defines the energy resolution of the spectrometer. Electrons passed into the energy analyser through the input slit 61 are resolved radially according to their energies and the circumferential diffraction image at the input aperture is preserved by virtue by its being oriented along the non-energy-dispersive circumferential direction of the energy analyser and is projected as an inverted image (due to the double-focusing action of the analyser) onto the analyser image plane 9. Thus, a two-dimensional electron image 79 is projected onto the image plane of the analyser having the general form of an annulus segment with electrons being separated according to their energy in the radial direction and according to their emission angle circumferentially. The electron image is detected by a two-dimensional position detector 65 which enables energy spectra over a range of emission angles to be measured simultaneously.

From the angle-resolved energy spectra the identity of the chemical elements at a particular point on the surface and as a function of depth below the surface can be determined. A manipulator can then be used to scan the sample transverse to the objective lens axis, for example in one or two dimensions to obtain information on the chemical elements and their depth profile over the sample surface. In this way, a four-dimensional image of the chemical constituents at each point in a selected near surface volume of the sample can be obtained.

As an alternative or in addition to mechanical manipulation, the surface of the sample may be scanned using electrostatic field deflector electrodes positioned transverse to the beam path between the sample and energy analyser. Although additional electrodes, for example plate electrodes, can be used in addition to those shown in the pre-analysis lens arrangement described above and shown in FIGS. 1 and 2, in one embodiment, the electrodes 47, 49, 51, 53 of the middle electrode section of the second lens 19 may be advantageously employed for this purpose. For example, in order to scan the surface of the sample in the z direction, a potential difference may be applied across the electrode segments 47, 51 which are opposed in this direction. In order to scan the sample surface in the x direction, a potential difference may likewise be applied across the electrode segments 49, 53 which are opposed in the x direction. Thus, advantageously, scanning of the sample surface may be achieved without mechanical manipulation of the sample and without additional deflector elements. Advantageously, scanning using deflector electrodes may be accompanied by scanning of the spot of the incident beam of photons or charged particles over the sample surface so that the viewed and irradiated area of the sample optimally coincide to provide optimised collection efficiency. Appropriate biasing of the deflector electrodes may also be used to correct for misalignment between the irradiated spot on the sample surface and the lens axis.

Figure 3A:
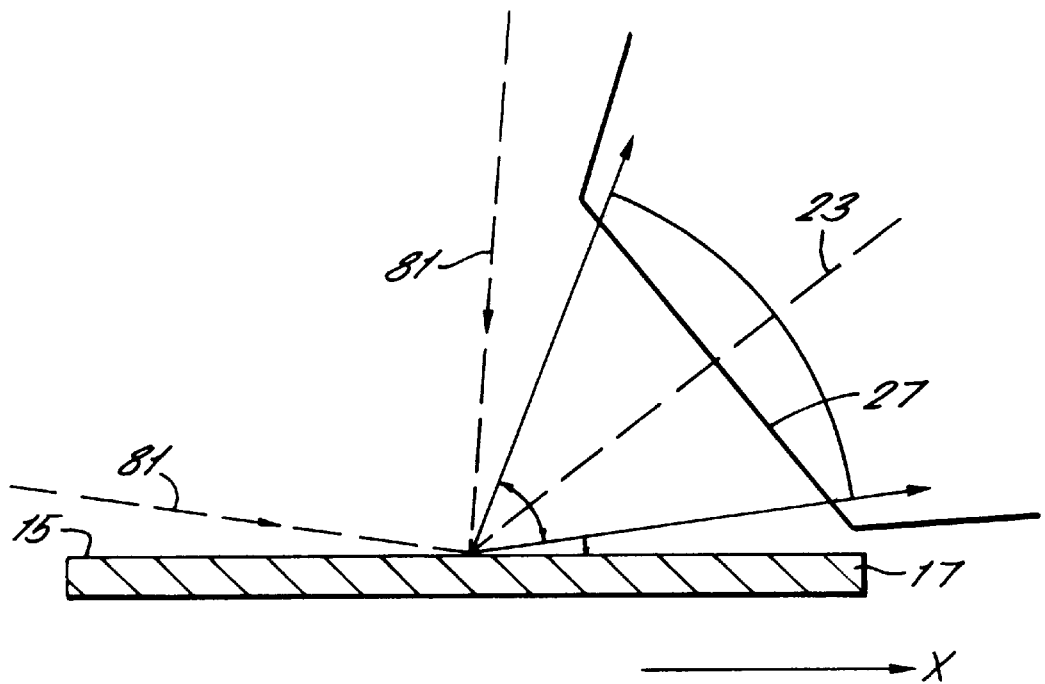
FIG. 3A shows an example of the geometry between the lens axis and the surface of a sample collecting charged particles over a range of emission angles.
Figure 3B:
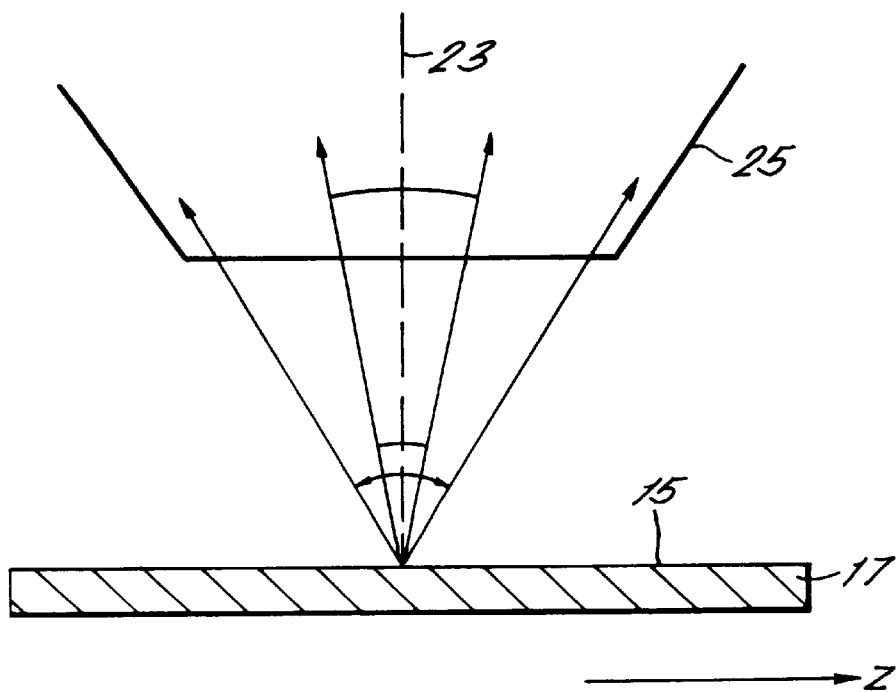
FIG. 3B shows an example of the geometry between the lens axis and the surface of a sample of FIG. 3A and an example of the range of emission angles used in the measurement of each energy spectra.

In order to obtain parallel spectra over emission angles ranging from near normal to the surface to near grazing, the lens axis may be inclined at an angle to the sample surface and the sample and/or pre-analysis lens may be tilted relative to the other. FIGS. 3A and 3B show an example of the relative geometry between a sample and the objective lens in which FIG. 3A is a side view of the geometry corresponding to the orientation of FIG. 2 and FIG. 3B is a side view of the same geometry rotated through 90°, i.e. in the same orientation as FIG. 1.

Referring to FIG. 3A, the objective lens is arranged such that the lens axis 23 is angled at 37° to the surface 15 of the sample 17. The objective lens is positioned from the sample surface and the input aperture 27 is sufficiently wide so that the objective lens can accept electrons or other charged particles emerging from the surface over a solid cone angle of about 60°. Thus, by tilting the lens axis relative to the sample surface by about 37°, electrons or other charged particles emerging from angles from between about 7° to 67° relative to the surface can be collected simultaneously. In order to collect charged particles emitted at angles larger than 67°, the angle between the lens axis and the sample surface can be increased. The geometry shown in FIG. 3A also provides extremely good access to the sample surface, particularly on the left-hand side of the figure for example to allow the direction of the irradiating beam line 81 to make an angle with the sample surface of beyond normal to very small grazing angles.

The combination of the objective lens which has a large acceptance angle and the input slit 61 of the energy analyser which has a large dimension in the non-energy-dispersive direction ensures that electrons having an angular distribution of approximately 60° as shown in FIG. 3A will be detected at the analyser image plane.

Referring to FIG. 3B, the objective lens is oriented such that the lens axis 23 is normal to the sample surface in the z direction shown in FIG. 1. In this direction, the objective lens also collects electrons or other charged particles emitted over a solid cone of half-angle 30° but over emission angles of greater than 60° relative to the sample surface. However, due to the low acceptance angle of the analyser input slit in the energy dispersive direction, the analyser will only pass electrons emitted from the sample surface over a smaller range of angles which also strongly depends on the retardation field applied to the electrons to reduce their energies to the pass energy of the analyser. This smaller range of emission angles may be, for example, between +10° to −10° normal to the surface in the energy dispersive direction, as shown in FIG. 3B. Thus, for each emission angle shown in FIG. 3A, the analyser is capable of passing electrons emitted over approximately 20° in the orthogonal direction shown in FIG. 3B. The range of angles over which electrons are collected in the energy dispersive direction provides sufficient numbers for good sensitivity in measuring the energy spectra.

Figure 4:
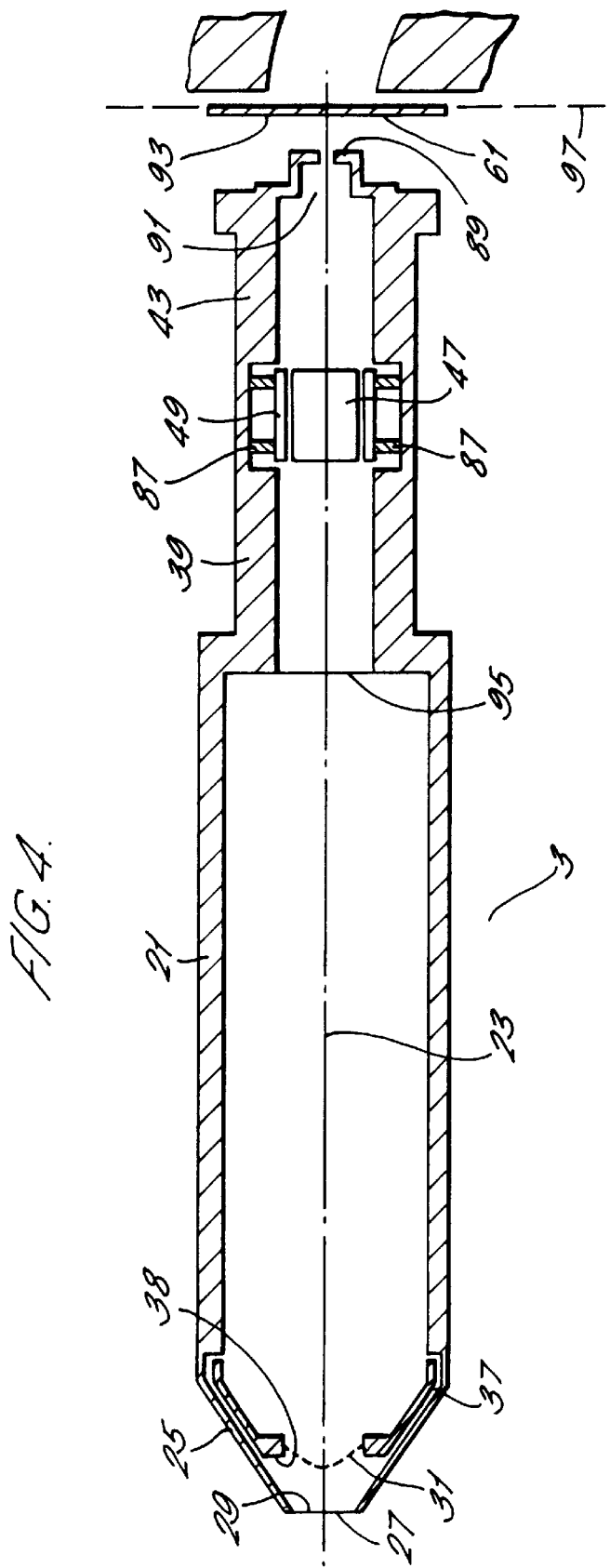
FIG. 4 shows a cross-sectional view of an embodiment of a pre-analysis lens arrangement.

FIGS. 4 and 5 show a cross-sectional view through an embodiment of the pre-analysis lens apparatus which is drawn to scale. The objective lens 13 comprises similar elements to those described above in relation to FIGS. 1 and 2 and similar elements are designated by the same reference numerals. Briefly, the objective lens which is shown in more detail in FIG. 5 comprises a conical section 25 defining an input aperture 27, a curved mesh element 33 positioned upstream of and being convex towards the input aperture 27 and an annular ring element 38 adjoining and supporting the convex mesh element 31, a truncated conical inner electrode 37 located substantially within the conical section 25 and upstream of and adjoining the mesh element 31 and a cylindrical electrode element 21 upstream of the inner conical element 37. In this embodiment, the convex mesh element 31 is shaped so that the angle of the surface of the mesh makes with a line 34 transverse to the lens axis 23 gradually decreases towards the outer part 36 of the mesh element 31 to generate a progressively weaker focusing field in this outer region, away from the lens axis. (This is similar in effect to the annular mesh portion 35 shown in FIGS. 1 and 2). Thus, the main difference between the objective lens shown in FIGS. 4 and 5 and that shown in FIGS. 1 and 2 is that the inner cylindrical electrode 37 tapers outwardly from the mesh element 31 away from the input aperture 27 in the embodiments shown in FIGS. 4 and 5. This ensures that the electrode elements downstream of the convex mesh element 31 provide a sufficiently large diameter to accommodate the electron stream with a reasonable filling factor, as will be described below with reference to FIG. 6.

Referring to FIG. 4, the second lens of the pre-analysis lens apparatus 3 is also shown and again comprises similar elements to those shown in FIGS. 1 and 2 and similar elements are designated by the same reference numerals. The first cylindrical electrode element 39 of the second lens is electrically connected to the cylindrical electrode 21 of the objective lens and is also connected to the third cylindrical electrode element 43 of the second lens. The quadrant elements of the middle electrode section of the second lens 47, 49, 51, 53 are mounted within a recess defined by the first and third cylindrical electrode elements 39, 43 and are electrically isolated therefrom by stand-offs 87. An electrode element 89 is positioned across the output 91 of the third lens element and a second electrode element 93 is positioned across the input slit 61 of the energy analyser. The first and second electrode elements 89, 93 are suitably apertured to allow electrons to pass therethrough and may for example comprise mesh or plate electrodes as well as others. The second electrode element 93 is biased, as necessary, with respect to the first electrode element 89 to control the kinetic energy of charged particles passed through the lens so as to match the pass energy of the analyser. The retarding field applied between the first and second electrode tends to refract charged particles entering the field at an angle to the lens axis to a greater angle. However such refraction does not cause significant reduction in the non-energy-dispersive direction in electrons passing into the analyser since, in this direction, the input aperture has a very large acceptance angle. Therefore, the effect of the retarding field in increasing the angular spread (i.e. divergence) of the electrons in the non-energy-dispersive direction before entering the analyser has little or no effect in reducing the sensitivity of the analyser. Furthermore, since spatial information of the sample is represented as angular information in the diffraction image and the angle of acceptance of the analyser for the diffraction image is very large, the field of view in the non-energy-dispersive direction does not change with retardation field. Advantageously, this allows alignment between the irradiated spot on the sample surface and the lens axis to be not too critical. The approximate position of the focal point of the objective lens is shown in FIG. 4 by reference numeral 95 for a lens constant β of 2.2.

Advantageously, the provision of two lenses in the pre-analysis lens allows chromatic aberration attributable to each lens separately to be compensated by the other over a range of energies so that an achromatic plane exists at the output of the second lens.

The spatial image in the energy dispersive direction and the diffraction image in the non-energy-dispersive direction projected by the second lens are preferably arranged to coincide with the achromatic plane 97 of the pre-analysis lens. This helps to ensure that in the energy-dispersive direction, electrons with energies ranging over the whole of the pass band energy of the analyser are all focused at the same plane, so that all electrons in the energy band are imaged at the image plane of the analyser, with no reduction in the ability of the spectrometer to collect electrons either side of the centre energy.

Projecting the diffraction image of the sample surface onto an achromatic plane ensures that each point on the plane solely represents a unique emission angle and is independent of electron energy.

FIG. 6 shows a computer generated, two-dimensional ray diagram showing the trajectories of electrons through an embodiment of the objective lens shown in FIG. 5. The objective lens elements which provide the boundary conditions are designated by the same reference numerals as those shown in FIGS. 4 and 5. The convex mesh electrode 31 and inner conical electrode 37 are biased at 2.2 times the electron energy and the outer conical section 25 defining the input aperture and the cylindrical electrode 21 are maintained at ground potential. In this example, a flat mesh element 29 is placed across the input aperture 27.

Electrons emitted over a 60° range of emission angles enter the input aperture 27 and are accelerated by the electric field between the flat mesh element 27 and the convex mesh electrode 31. The geometry of the conical input section 25 generates a relatively large electric field component transverse to the lens axis near its surface as shown by the equipotential lines in region A. This field component strongly opposes divergence of electrons adjacent the edge of the stream such that their trajectories tend to align rapidly with the lens axis which assists in minimising the stream width. At the same time, the electric field lines generated by and near the less curved outer edge portion 36 of the convex mesh electrode 31 are substantially parallel to the lens axis as shown by the equipotential lines in region B. This weakening of the focusing field near the edge of the convex mesh electrode serves to correct for spherical aberration of the outermost electrons in the stream. Note that the converse effect is true for electrons near the centre of the stream, where electrons are subjected to a stronger focusing field near the convex mesh than near the flat mesh at the input 27. Electrons passing through the convex mesh are subsequently focused to the focal plane 95 of the objective lens by the electric field between the cylindrical electrode 21 and the inner conical electrode 37. The accelerating field between the input aperture and the convex mesh electrode correct for chromatic aberration so that electrons having energies in the pass band range of the energy analyser are sharply focused.

Although the pre-analysis lens described above is arranged to project a real image of the sample in the energy-dispersive direction of the analyser in another embodiment, the lens may be arranged to project a diffraction image along the energy-dispersive direction (as well as the non-energy-dispersive direction). However, the projection of a real image in the energy-dispersive direction is preferred since the real image contains a higher density of electrons than the diffraction image so that more electrons can be passed into the analyser for a given slit width.

In another embodiment, another lens arrangement may be provided at the output of the analyser arranged to project the image formed at the analyser image plane to another image plane, and the detector may be arranged to detect the image formed at this other image plane.

In another embodiment, the pre-analysis lens may be arranged to project a real image of the sample in the non-energy-dispersive direction on the input plane of the analyser and another lens may be arranged to project a diffraction image of the image at the output plane of the analyser onto a detector, in which the diffraction image of that image is in the non-energy-dispersive direction.

The second lens of the pre-analysis lens may be arranged to magnify the image at its object plane.

Any form of energy analyser may be used, including electrostatic, e.g. toroidal capacitor or retarding-type analysers and magnetic energy analysers.

Modifications to the embodiments described above will be apparent to those skilled in the art.

We claim:

1. A spectrometer comprising an energy analyser for analysing energies of charged particles emitted from an analysis area of a sample, a lens arranged to project a diffraction image of at least part of said analysis area at the image plane of said lens, and a detector for detecting said charged particles, wherein said analyser and lens are arranged to generate an image at said detector in which said charged particles are distributed along a first direction of said image according to their emission angles and said charged particles are distributed along a second direction of said image according to their energies, said detector being arranged to detect the distribution of charged particles along said first direction.

2. A spectrometer as claimed in claim 1, wherein said analyser has an object plane, an image plane, and an energy dispersive axis, and said lens is arranged to project said charged particles onto said object plane as a real image of at least part of said analysis area substantially in the direction of said axis and as a diffraction image of said at least part of said analysis area substantially along a non-energy-dispersive direction of said analyser.

3. A spectrometer as claimed in claim 2, wherein said lens is arranged to project said real and diffraction images onto said object plane such that, at said object plane, said real image is substantially perpendicular to said diffraction image.

4. A spectrometer as claimed in claim 1, wherein said lens comprises an electrostatic lens.

5. A spectrometer as claimed in claim 4, wherein said lens includes a quadrupole lens.

6. A spectrometer as claimed in claim 5, wherein said lens comprises first, second, third and fourth electrodes defining a passage through which said charged particles can pass wherein said first and second electrodes are opposed in a direction along said axis and said third and fourth electrodes are opposed in a direction perpendicular to said axis, said lens further comprising electrode means extending beyond each end of the passage defined by said electrodes for forming an electrostatic field therewith.

7. A spectrometer as claimed in claim 6, wherein said electrode means comprises a cylindrical electrode.

8. A spectrometer as claimed in claim 6, wherein at least one of said electrodes is formed as a segment of a cylinder.

9. A spectrometer as claimed in claim 1, wherein said energy analyser comprises an electrostatic sector analyser.

10. A spectrometer as claimed in claim 9, wherein said energy analyser comprises a hemispherical sector analyser.

11. A spectrometer as claimed in claim 1 further comprising a second lens arranged to receive charged particles from said analysis area and transfer charged particles to said lens.

12. A spectrometer as claimed in claim 11, wherein said second lens comprises a lens for collecting and focusing a divergent stream of charged particles comprising means defining an input aperture for receiving said divergent stream, a lens axis extending through said input aperture, first electrode means, second electrode means spaced from said first electrode means along said lens axis and comprising a multi-apertured electrically conductive web arranged to allow charged particles in said stream to pass therethrough, wherein a portion of the surface of said electrically conductive web is spaced from and arranged to converge towards said lens axis in a direction towards said input aperture thereby to provide an electric field component which opposes divergence of said stream when a potential difference is applied between said first and second electrode means to accelerate said charged particles towards said second electrode means.

13. A spectrometer as claimed in claim 12, wherein said first electrode means defines a surface which converges towards said axis in a direction towards said input aperture.

14. A spectrometer as claimed in claim 13 wherein said convergent surface of said first electrode means is arranged opposite at least part of said further portion in a direction parallel to said axis.

15. A spectrometer as claimed in claim 13, wherein said convergent portion of said first electrode means extends to a position adjacent said input aperture.

16. A spectrometer as claimed in claim 12, wherein said first electrode means comprises a multi-apertured conductive web arranged to allow charged particles in said stream to pass therethrough.

17. A spectrometer as claimed in claim 16, wherein said multi-apertured conductive web of said first electrode means is disposed transverse to said lens axis and adjacent said input aperture.

18. A spectrometer as claimed in claim 17, wherein said web of said first electrode means defines a surface towards said second electrode means which is substantially flat.

19. A spectrometer as claimed in claim 12, wherein said web of said second electrode means defines a convex surface directed towards said input aperture.

20. A spectrometer as claimed in claim 12, wherein said first and second electrode means are arranged such that the strength of the electric field component transverse to said lens axis which acts upon charged particles adjacent the edge of said stream is greater proximate said first electrode means than proximate said second electrode means.

21. A spectrometer as claimed in claim 12, wherein the convergent portion of said second electrode means is disposed opposite said input aperture in a direction parallel to said lens axis.

22. A spectrometer as claimed in claim 12, wherein at least one of said first and second electrode means is rotationally symmetric about said lens axis.

23. A spectrometer as claimed in claim 12, wherein said first electrode means defines a generally frusto-conical surface.

24. A spectrometer as claimed in claim 12, including further electrode means disposed downstream of said second electrode means for defining an electric field for causing said stream to converge to a focus on application of a potential difference between said second electrode means and said further electrode means.

25. A spectrometer as claimed in claim 12, wherein said further electrode means defines a generally cylindrical inner surface which is concentric with said lens axis.

26. A spectrometer as claimed in claim 12, wherein said electrically conductive web of said second electrode means extends across said lens area.

27. A spectrometer as claimed in claim 12, wherein said electrically conductive web is substantially parabolic with its axis of symmetry coaxial with said lens axis.

28. A method of measuring energy spectra of charged particles emitted from a surface over a range of emission angles comprising, the steps of (a) forming a diffraction image of said charged particles, (b) resolving said charged particles spatially according to their energies, where steps (a) and (b) are performed in either order and (c) forming an image of said charged particles in which said charged particles are distributed in a first direction according to their emission angles and in a second direction according to their energies, and (d) deriving from said image angle-resolved energy spectra of said charged particles.

29. A lens for collecting and focusing a divergent stream of charged particles comprising means defining an input aperture for receiving said divergent stream, a lens axis extending through said input aperture, first electrode means, second electrode means spaced from said first electrode means along said lens axis and comprising a multi-apertured electrically conductive web arranged to allow charged particles in said stream to pass therethrough, wherein a portion of the surface of said electrically conductive web is spaced from and arranged to converge towards said lens axis in a direction towards said input aperture thereby to provide an electric field component which opposes divergence of said stream when a potential difference is applied between said first and second electrode means to accelerate said charged particles towards said second electrode means.

30. A lens as claimed in claim 29, wherein said first electrode means defines a surface which converges towards said axis in a direction towards said input aperture.

31. A lens as claimed in claim 30, wherein said convergent surface of said first electrode means is arranged opposite at least part of said further portion in a direction parallel to said axis.

32. A lens as claimed in claim 30, wherein said convergent portion of said first electrode means extends to a position adjacent said input aperture.

33. A lens as claimed in claim 29, wherein said first electrode means comprises a multi-apertured conductive web arranged to allow charged particles in said stream to pass therethrough.

34. A lens as claimed in claim 33, wherein multi-apertured conductive web of said first electrode means is disposed transverse to said lens axis and adjacent said input aperture.

35. A lens as claimed in claim 34, wherein said web of said first electrode means defines a surface towards said second electrode means which is substantially flat.

36. A lens as claimed in claim 29, wherein said web of said second electrode means defines a convex surface directed towards said input aperture.

37. A lens as claimed in claim 29, wherein said first and second electrode means are arranged such that the strength of the electric field component transverse to said lens axis which acts upon charged particles adjacent the edge of said stream is greater proximate said first electrode means than proximate said second electrode means.

38. A lens as claimed in claim 29, wherein the in-convergent portion of said second electrode means is disposed opposite said input aperture in a direction parallel to said lens axis.

39. A lens as claimed in claim 29, wherein at least one of said first and second electrode means is rotationally symmetric about said lens axis.

40. A lens as claimed in claim 29, wherein said first electrode means defines a generally frusto-conical surface.

41. A lens as claimed in claim 29, including further electrode means disposed downstream of said second electrode means for defining an electric field for causing said stream to converge to a focus on application of a potential difference between said second electrode means and said further electrode means.

42. A lens as claimed in claim 41, wherein said further electrode means defines a generally cylindrical inner surface which is concentric with said lens axis.

43. A lens as claimed in claim 29, wherein said electrically conductive web of said second electrode means extends across said lens area.

44. A lens as claimed in claim 29, wherein said electrically conductive web is substantially parabolic with its axis of symmetry coaxial with said lens axis.

* * * * *